(12) United States Patent
May et al.

(10) Patent No.: US 7,575,767 B2
(45) Date of Patent: Aug. 18, 2009

(54) EXTRACTION OF PALM VITAMIN E, PHYTOSTEROLS AND SQUALENE FROM PALM OIL

(75) Inventors: Choo Yuen May, Selengor (MY); Harrison Lau Lik Nang, Selengor (MY); Ma Ah Ngan, Selengor (MY); Yusof Basiron, Selengor (MY)

(73) Assignee: Malaysian Palm Oil Board, Selangor (MY)

( * ) Notice: Subject to any disclaimer, the term of this patent is extended or adjusted under 35 U.S.C. 154(b) by 303 days.

(21) Appl. No.: 10/642,596

(22) Filed: Aug. 19, 2003

(65) Prior Publication Data

US 2005/0250953 A1   Nov. 10, 2005

(30) Foreign Application Priority Data

Aug. 20, 2002   (MY) .............. PI 2002 3069

(51) Int. Cl.
*A01N 65/00*   (2006.01)
*A61K 36/00*   (2006.01)
*A01N 61/00*   (2006.01)
*A61K 31/00*   (2006.01)
*A61K 31/355*  (2006.01)

(52) U.S. Cl. ................ 424/776; 514/1; 514/458
(58) Field of Classification Search ......... 426/494; 203/43, 74, 80, 81; 424/439, 725; 549/413
See application file for complete search history.

(56) References Cited

U.S. PATENT DOCUMENTS

| | | | | |
|---|---|---|---|---|
| 2,598,269 A | * | 5/1952 | Kirschenbauer | 552/545 |
| 2,729,655 A | | 1/1956 | Charles et al. | |
| 2,741,644 A | * | 4/1956 | Blaizot | 203/38 |
| 4,550,183 A | * | 10/1985 | Willging | 549/413 |
| 5,487,817 A | * | 1/1996 | Fizet | 203/38 |
| 5,646,311 A | * | 7/1997 | Hunt et al. | 549/413 |
| 5,660,691 A | * | 8/1997 | Barnicki et al. | 203/72 |
| 5,902,890 A | * | 5/1999 | Nitsche et al. | 554/174 |
| 6,057,462 A | * | 5/2000 | Robinson et al. | 552/545 |
| 6,838,104 B2 | * | 1/2005 | Jacobs | 426/494 |

FOREIGN PATENT DOCUMENTS

| | | |
|---|---|---|
| EP | 0 541 999 A1 | 5/1993 |
| EP | 0992499 A2 | 4/2000 |
| EP | 1097985 A1 | 5/2001 |
| EP | 1394144 B1 | 4/2006 |
| GB | 531224 | 12/1940 |
| GB | 531226 | 12/1940 |
| GB | 549931 | 12/1942 |
| JP | 09176057 A * | 7/1997 |
| WO | WO-00/09535 A1 | 2/2000 |
| WO | WO-01/32682 A1 | 5/2001 |
| WO | WO 0132682 A1 * | 5/2001 |

OTHER PUBLICATIONS

Ruengwit et al., "Methyl Ester from Palm Oil: Optimization of transesterification using sodium hydroxide and alumina as catalyst". (2001) Abstract.*
European Search report App # 03 255 148.3 (Oct. 19, 2004).
Choo et al., "Recovered Oil from Palm-Pressed Fiber: A Good Source of Natural Carotenoids, Vitamin E, and Sterols," XP 000647324, AOCS, vol. 73, No. 5 (1996), pp. 599-602.

* cited by examiner

*Primary Examiner*—Christopher R Tate
*Assistant Examiner*—Amy L Clark
(74) *Attorney, Agent, or Firm*—Birch, Stewart, Kolasch & Birch, LLP

(57) ABSTRACT

Phytosterols, squalene and Vitamin E are recovered from phytonutrients concentrate derived from crude palm oil by the disclosed invention via esterification, transesterification, vacuum distillation, saponification, crystallization and organic solvents partitioning. Crude palm oil is subjected to esterification and transesterification for the production of crude palm oil methyl esters. Phytonutrients concentrate containing phytosterols, squalene, Vitamin E and unreacted monoglycerides is recovered from crude palm oil methyl esters by multi-stages vacuum distillation in which components with higher molecular weight are filtered during second stage vacuum distillation. The purified phytonutrients concentrate is subjected to saponification process and the unsaponifiable matter is added to a combination of solvents for crystallization of phytosterols. The filtrate enriched in squalene and Vitamin E is separated to its individual squalene-rich layer and vitamin E-rich layer via organic solvents partitioning.

14 Claims, 2 Drawing Sheets

EXTRACTION OF PALM VITAMIN E, PHYTOSTEROLS AND SQUALENE FROM PALM OIL

This nonprovisional application claims priority under 35 U.S.C. 119(a) on Patent Application No(s). PI 20023069 filed in Malaysia on Aug. 20, 2002, which is(are) herein incorporated by reference.

FIELD OF INVENTION

The invention relates to the extraction of phytosterols, squalene and vitamin E form crude palm oil. More particularly the present invention relates to an integrated process to extract phytosterols, squalene and vitamin E from crude palm oil.

BACKGROUND OF THE INVENTION

Palm oil contains 700-1000 ppm of vitamin E, 300-620 ppm of phytosterols and 250-730 ppm of squalene. The present invention relates to a process for the recovery of the natural occurring Vitamin E, phytosterols and squalene from crude palm oil.

Vitamin E is a group of natural occurring lipid soluble antioxidants, namely tocopherols and tocotrienols that are found in certain vegetable oils. The main occurrence of tocotrienols is in palm oil, wheat germ oil, coconut oil and corn oil. Tocotrienols possess higher antioxidant activity than tocopherols, which have been shown in biochemical studies (Serbinova et al., 1991, Pokorny, J 1987 and Jacobsberg et al 1978). As a predominant type of vitamin E constituting 80% of total vitamin E found in palm oil, tocotrienols have also been known to possess hypocholesteolemic effect (Tan et al 1991 and Qureshi et al 1991).

Phytosterols are structurally similar to cholesterol except they are alkylated at the 24 position in the side chain. The most abundant type of phytosterols by far found in plants are β-sitosterol, stigmasterol and campesterol. These compounds are natural components of diet and are consumed in amounts of 100-500 mg/day with respect to US consumption (Weirauch, J L Gradner, J M 1978. Sterol content of foods of plant origin. J Am, Diet. Assoc. 73:39-47). Studies conducted employing β-sitosterol were found to significantly reduce the amount of cholesterol in the blood (Farguhar, J W et al 1956. Circulation, 14, 77-82). Palm oil is rich in phytosterols with 60% of β-sitosterol and the remaining 38% is stigmasterol and campesterol. Therefore it provides a natural source of phytosterols for recovery.

Squalene is a major component in various deep-sea shark liver oils. It is a powerful antioxidant that can scavenge free radicals from the body before they start their debilitating effect. Trials have shown that where squalene is taken as a dietary supplement, evidence has shown that it has preventative effects against carcinogenesis.

Squalene presents as one of the minor components in palm oil. It could be recovered as a valuable antioxidant if presented in high concentration.

The related patents which have been filed include WO0009535, GB 531226, GB 549931, GB 531224 and EP 0541999. These patents concentrate in the recovery of vitamin E or vitamin E and phytosterols but not as an integrated process for the recovery of vitamin E, phytosterols and squalene together as described in this invention. The patented inventions only proceed with one stage vacuum distillation in which it does not serve for the removal of high molecular weight components as described in this invention. Therefore, it is an objective of this invention to provide a method for purifying and recovering of these valuable minor compounds namely vitamin E, phytosterols and squalene to their respective fractions with crystallized phytosterols at high purity.

SUMMARY OF THE INVENTION

The invention relates to an integrated process for the recovery of valuable palm oil phytonutrients more particularly vitamin E, phytosterols and squalene which comprises the steps of acid/alkaline catalysed esterification/transesterificaton process of palm oil with lower alkyl alcohol, multi-stage vacuum distillation of alkyl esters, saponification of the phytonutrients concentrate, crystallization of phytosterols and finally partitioning of vitamin E and squalene with organic solvents.

Crude palm oil was esterified in alkyl alcohol preferably methanol and ethanol using sodium hydroxide or potassium hydroxide as catalyst to substitute the glycerol portion of glycerides with alkyl groups for the production of alkyl esters and glycerol. The type of alkyl alcohols used depending on the volatility of the alkyl esters produced in which the lower boiling point alkyl esters with shorter alkyl chain length are preferable in this case.

The lower boiling alkyl esters were subjected to multistage vacuum distillation, preferably three stage short path distillation (SPD) at different operating conditions as described below. The first short path distillation served the purpose to distill about 90% of the bulk esters with minimal amount of vitamin E, phytosterols and squalene being distilled over to the distillate. The applied short path distillation conditions are temperature ranging from 70° C. to 120° C. and pressure ranging from 10 mTorr to 50 mTorr. The phytonutrients enriched residue was then subjected to second short path distillation in the removal of all the impurities and colouring materials/pigments including carotenes, phospholipids, glycolipids, waxes, oxidized products and other long chain hydrocarbons. The operating conditions are temperature ranging from 130° C. to 200° C. and pressure less than 1 mTorr. The distillate from the second short path distillation was subsequently subjected to the third short path distillation to produce vitamin E, phytosterols, squalene and monoglycerides concentrates in a mixture with operating temperature less than 130° C. and pressure less than 1 mTorr. The purified concentrate is free from all indigenous heavy molecules which is critical in the following separation and purification processes.

To the purified concentrate, saponification process was carried out in the presence of hydroxide and alcohol. They hydroxides used are sodium hydroxide and potassium hydroxide whereas alcohols used including methanol, ethanol and iso-propanol. The unsaponifiable materials were recovered using hydrocarbon solvents extraction of the reaction mixture such as heptane, hexane, iso-octane and petroleum ether. The hydrocarbon layer was neutralized with copious of water washing and the unsaponifiable matters recovered containing only vitamin E, phytosterols and squalene.

Phytosterols were crystallized out from the unsaponifiable mixture using water/alcohol/hydrocarbon system by heating and cooling processes preferably from 70° C.-85° C. to 25° C.-35° C. The crystallized phytosterols were filtered and to the remaining part of the mixture, hydrocarbon solvent and alkyl alcohol was introduced to partitioning the less polar squalene into hydrocarbon layer and the relatively more polar vitamin E into the alkyl alcohol layer. The alkyl alcohols used including methanol and ethanol and hydrocarbon solvents used including hexane, heptane and iso-octane.

DETAILED DESCRIPTION OF THE INVENTION

Figure 1:
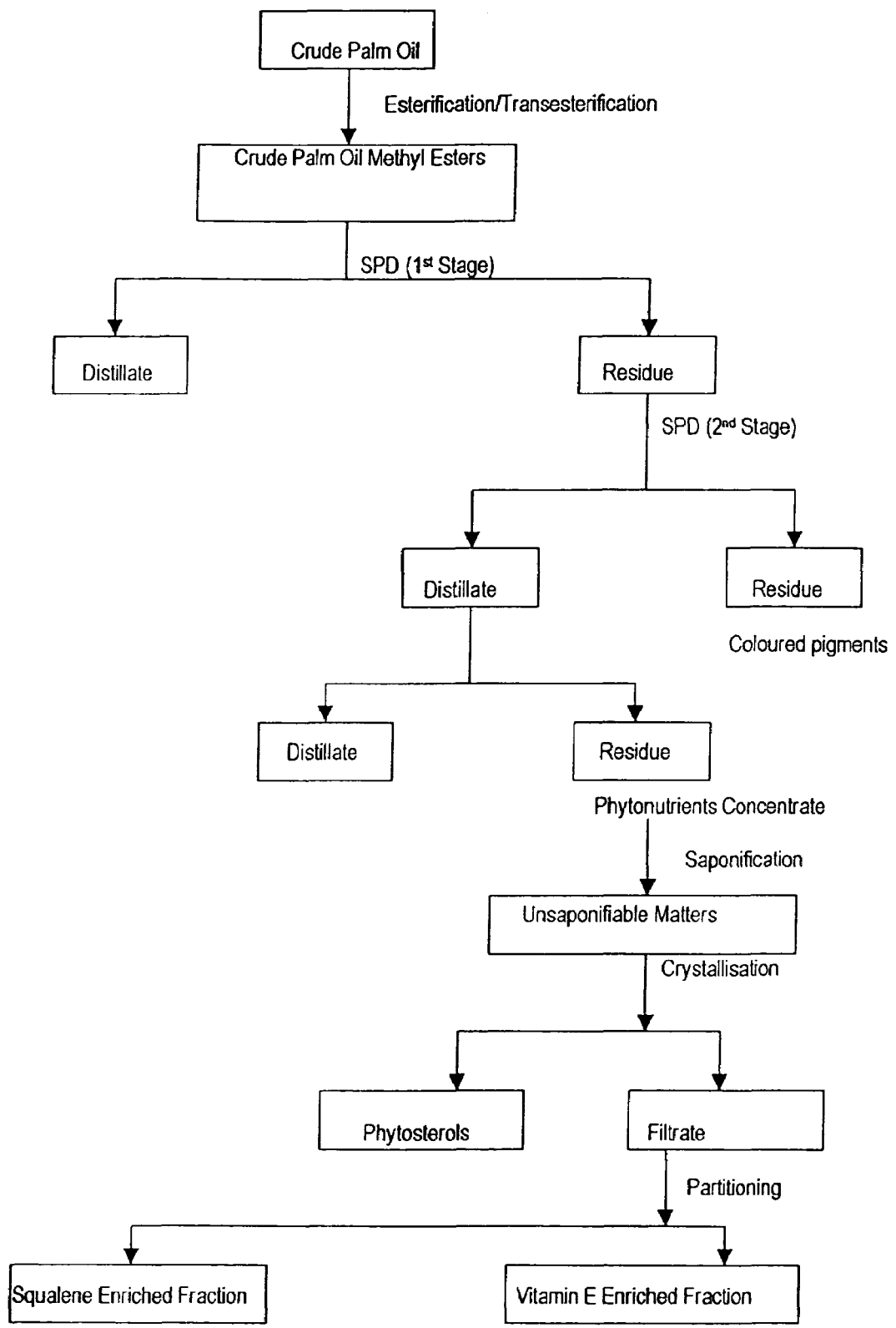
FIG. 1 shows a schematic representation of the extraction process of the phytonutrients concentrate.

The invention will now be described with reference to FIG. 1 and to the following steps as example of the steps involved in the extraction process. The quantities used and parameters used are by way of example only and are not limited thereto unless otherwise stated.

Example 1

5 kg of crude palm oil was esterified with 2.5 kg of methanol and 50 g of NaOH as catalyst. The methyl esters were separated from glycerol and neutralized by water washing. Methyl esters were subjected to the first short path distillation at temperature of 90° C. and pressure of 20 mTorr. The residue was then subjected to second short path distillation under operating temperature of 150° C. and pressure of 1 mTorr to remove all coloured materials/pigments. The light yellowish distillate was subsequently subjected to third short path distillation with temperature of 90° C. and pressure of 1 mTorr for the production of vitamin E, phytosterols and squalene (phytonutrients) concentrates. The detailed analysis results of the phytonutrients concentrates are shown in Table 1.

Example 2

3 grams of the purified phytonutrients concentrates as obtained from Example 1 or from other sources was saponified using 5 ml of 10% KOH and 20 ml of ethanol. The mixture was refluxed under nitrogen blanketing for 30 minutes. The reacted mixture was transferred into a separating funnel with 10 ml of ethanol, 20 ml of hot distilled water and 30 ml of hexane. The mixture was shaken and cooled to room temperature leaving hexane layer at the top and aqueous layer at the bottom. The unsaponifiable materials, which is hexane soluble was collected from the top whereas the aqueous layer was further extracted 5 times with 30 ml hexane/water of ratio 9:1. The hexane layer recovered was neutralized with water washing and all the solvents was removed by rotary-evaporator and vacuum pump drying. Recovery of vitamin E, phytosterols and squalene are 83%, 93% and 86%. The detailed analysis results are shown in Table 2.

Example 3

0.42 grams of the unsaponifiable materials from saponification of purified phytonutrients concentrates as obtained from Example 2 or from other sources was added with 5 ml of ethanol, 5 ml of hexane and 0.5 ml of distilled water. The mixture was shaken to a homogeneous stage and settled into two layers. The hexane layer at the top was separated from the ethanol/water layer at the bottom. Solvents were removed using rotary-evaporator and vacuum pump dryer. The concentration of squalene in hexane layer is 41% with recovery of 97% and the concentration of sterols in ethanol layer is 64.7% with recovery of 52.9%. The concentration of vitamin E in hexane and ethanol layers is 12% and 20.4%. The detailed analysis results are shown in Table 3.

Example 4

0.8 grams of the unsaponifiable matters with phytosterols concentration of 39.4% from saponification of purified phytonutrients concentrates as obtained from Example 3 or from other sources was added with 2.5 ml hexane, 0.1 ml methanol and 0.1 ml distilled water. The mixture was heated to 70° C. and cooled slowly to 28° C. The solid crystal formed was filtered with suction and washed with copious amount of hexane. The solvents in the filtrate were rotary evaporated and vacuum pump dried. The concentration of phytosterols is 99% with recovery of 63.5%. The detailed analysis results are shown in Table 4.

Example 5

0.73 grams of the unsaponifiable matters with phytosterols concentration of 39.4% from saponification of purified phytonutrients concentrates was added as obtained from Example 4 or from other sources with 3.5 ml hexane, 0.1 ml methanol and 0.1 ml distilled water. The mixture was heated to 70° C. and cooled slowly to 28° C. The solid crystal formed was filtered with suction and washed with copious amount of hexane. The solvents in the filtrate were rotary evaporated and vacuum pump dried. The concentration of phytosterols is 99% with recovery of 41.7%. The detailed analysis results are shown in Table 5.

Example 6

0.69 grams of the unsaponifiable matters with phytosterols concentration of 39.4% from saponification of purified phytonutrients concentrates as obtained from Example 5 or from other sources was added with 2.5 ml hexane, 0.05 ml methanol and 0.1 ml distilled water. The mixture was heated to 70° C. and slowly cooled to 28° C. The solid crystal formed was filtered with suction and washed with copious amount of hexane. The solvents in the filtrate were rotary evaporated and vacuum pump dried. The concentration of phytosterols is 99% with recovery of 36.8%. The detailed analysis results are shown in Table 6.

Example 7

0.71 grams of the unsaponifiable matters with phytosterols concentration of 54.4% from saponification of purified phytonutrients concentrates as obtained from Example 6 or from other sources was added with 2.5 ml hexane, 0.1 ml methanol and 0.1 ml distilled water. The mixture was heated to 70° C. and slowly cooled to 28° C. The solid crystal formed was filtered with suction and washed with copious amount of hexane. The solvents in the filtrate were rotary evaporated and vacuum pump dried. The concentration of phytosterols is 99% with recovery of 41%. The detailed analysis results are shown in Table 7.

Example 8

0.29 grams of the filtrate obtained from Example 5 or other solvents after crystallisation of phytosterols was added with 5 ml hexane and 2 ml methanol. The mixture was shaken to a homogeneous stage and settled into two layers. The hexane layer at the top was separated from the methanol layer at the bottom. Solvents were removed using rotary-evaporator and vacuum pump dryer. The concentration of vitamin E in methanol layer is 31.3% with recovery of 52.6% and the concentration of squalene in hexane layer is 51% with recovery of 87.5%. The detailed analysis results are shown in Table 8.

Example 9

0.34 grams of the filtrate obtained from Example 7 or other solvents after crystallisation of phytosterols was added with 5 ml hexane and 3 ml methanol. The mixture was shaken to a homogeneous stage and settled into two layers. The hexane layer at the top was separated from the methanol layer at the bottom. Solvents were removed using rotary-evaporator and vacuum pump dryer. The concentration of vitamin E is 51.2% with recovery of 57.5% and the concentration of squalene in hexane layer is 44.2% with recovery of 95.4%. The detailed analysis results are shown in Table 9.

Example 10

Figure 2:
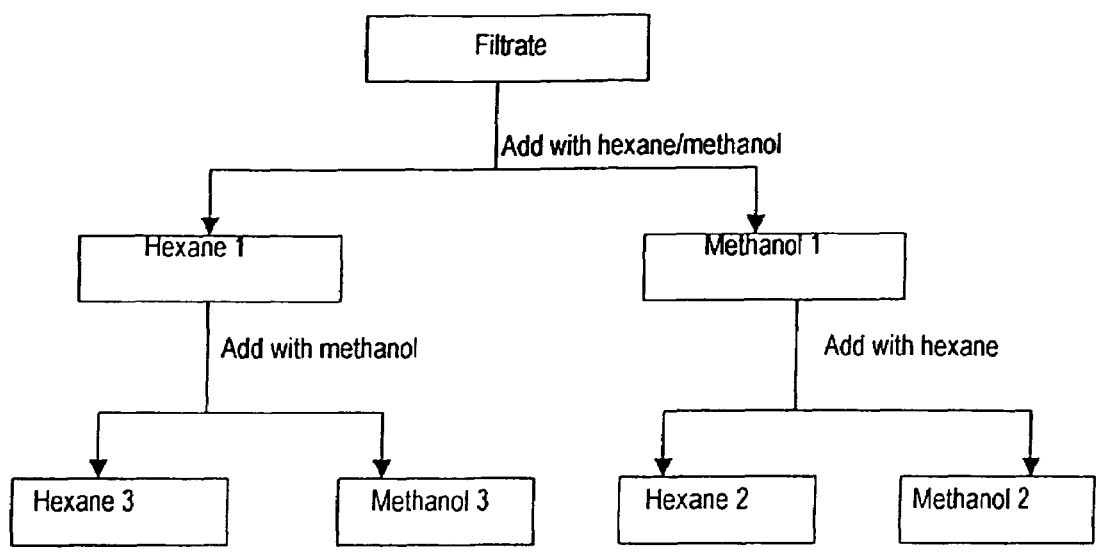
FIG. 2 shows a schematic representation of treating the filtrate of the unsaponifiable matters after crystallization of phytosterols from purified phytonutrients concentrate with serial partitioning of organic solvents to enhance the concentration of vitamin E and squalene.

The filtrate of the unsaponifiable matters after crystallisation of phytosterols from purified phytonutrients concentrate was treated with serial partitioning of organic solvents to enhance the concentration of vitamin E and squalene. 0.6 g of filtrate was added with 5 ml of hexane and 3 ml of methanol. The mixture was chilled to 15° C. for 15 minutes. The hexane layer was separated from methanol layer and analysed, 1ml of hexane was subsequently added to methanol layer and 1ml of methanol was added to hexane layer. After chilling to 15° C. for another 15 minutes, all the hexane and methanol layers were separated. All samples were analysed for vitamin E and squalene contents. The concentration of vitamin E in methanol phase after second partitioning of methanol layer is 79.3% with recovery of 34.9%. The concentration of squalene in hexane phase after second partitioning of hexane layer is 77.2% with recovery of 65.5%. The detailed analysis results are shown in Table 10. The process is described in FIG. 2.

TABLE 1

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Undetermined Products |
| Crude Palm Oil Methyl Esters | 0.00 | 98.13 | 1.11 | 0.22 | 0.06 | 0.07 | 0.06 | 0.05 | 0.06 | ND |
| Residue (1st Stage SPD) | 0.00 | 84.09 | 9.99 | 2.87 | 0.78 | 0.64 | 0.67 | 0.47 | 0.64 | ND |
| Residue (2nd Stage SPD) | 0.00 | 2.40 | 0.00 | 43.57 | 7.82 | 0.00 | 1.11 | 0.71 | 4.99 | 39.40 |
| Residue (3rd Stage SPD) | 0.00 | 5.78 | 53.69 | 3.94 | 0.53 | 6.56 | 8.40 | 3.98 | 0.12 | ND |
| Distillate (1st Stage SPD) | 0.00 | 99.00 | 0.05 | 0.00 | 0.00 | 0.00 | 0.00 | 0.01 | 0.00 | ND |
| Distillate (2nd Stage SPD) | 0.00 | 89.40 | 8.96 | 0.07 | 0.00 | 0.59 | 0.62 | 0.41 | 0.02 | ND |
| Distillate (3rd Stage SPD) | 0.00 | 98.33 | 0.25 | 0.00 | 0.00 | 0.00 | 0.00 | 0.01 | 0.00 | ND |

TABLE 2

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Purified Phytonutrients Conc | 0 | 4.48 | 66.33 | 0 | 1.04 | 6.39 | 15.06 | 6.66 | 0.05 | 3.03 |
| Unsaponifiable Materials | 3.8 | 0.0 | 0.0 | 0.0 | 2.5 | 20.5 | 52.4 | 20.7 | 0.2 | 0.81 |

TABLE 3

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Unsaponifiable Materials (Starting materials) | 3.6 | 0.0 | 0.0 | 0.0 | 2.9 | 25.5 | 49.5 | 18.2 | 0.1 | 0.42 |
| Hexane Layer | 2.3 | 0.0 | 0.0 | 0.0 | 4.9 | 41.0 | 39.7 | 12.0 | 0.1 | 0.26 |
| EtOH Layer | 5.3 | 0.0 | 0.0 | 0.0 | 0.3 | 9.3 | 64.7 | 20.4 | 0.1 | 0.17 |

TABLE 4

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Unsaponifiable Materials (Starting materials) | 8.8 | 0.0 | 0.0 | 0.3 | 3.2 | 33.7 | 39.4 | 14.1 | 0.3 | 0.79 |
| Filtrate | 11.3 | 0.0 | 0.0 | 0.5 | 3.9 | 46.9 | 18.4 | 17.2 | 0.5 | 0.61 |
| Solid | 0.0 | 0.0 | 0.0 | 0.0 | 0.0 | 0.0 | 100.0 | 0.0 | 0.0 | 0.19 |

TABLE 5

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Unsaponifiable Materials (Starting materials) | 8.8 | 0.0 | 0.0 | 0.3 | 3.2 | 33.7 | 39.4 | 14.1 | 0.3 | 0.73 |
| Filtrate | 10.7 | 0.0 | 0.0 | 0.6 | 4.2 | 43.2 | 24.6 | 16.2 | 0.4 | 0.61 |
| Solid | 0.0 | 0.0 | 0.0 | 0.0 | 0.0 | 0.0 | 100.0 | 0.0 | 0.0 | 0.12 |

TABLE 6

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Unsaponifiable Materials (Starting materials) | 8.8 | 0.0 | 0.0 | 0.3 | 3.2 | 33.7 | 39.4 | 14.1 | 0.3 | 0.69 |
| Filtrate | 10.0 | 0.0 | 0.0 | 0.4 | 3.5 | 41.0 | 28.9 | 15.7 | 0.3 | 0.59 |
| Solid | 0.0 | 0.0 | 0.0 | 0.0 | 0.0 | 0.0 | 100.0 | 0.0 | 0.0 | 0.10 |

TABLE 7

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Unsaponifiable Materials (Starting materials) | 1.8 | 0.0 | 0.0 | 0.0 | 2.5 | 18.5 | 54.4 | 22.7 | 0.2 | 0.71 |
| Crystallized Phytosterols | 0.0 | 0.0 | 0.0 | 0.0 | 0.0 | 0.0 | 99.0 | 0.0 | 0.0 | 0.16 |
| Filtrate | 3.0 | 0.0 | 0.0 | 0.0 | 4.8 | 30.0 | 35.9 | 26.2 | 0.2 | 0.55 |

TABLE 8

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Filtrate (Starting materials) | 11.7 | 0.0 | 0.0 | 0.0 | 3.7 | 42.2 | 21.4 | 16.4 | 0.5 | 0.29 |
| Hexane Layer | 11.3 | 0.0 | 0.0 | 0.4 | 4.6 | 51.0 | 17.4 | 10.3 | 0.5 | 0.21 |
| MeOH Layer | 10.2 | 0.0 | 0.0 | 0.0 | 1.7 | 23.6 | 33.0 | 31.3 | 0.3 | 0.08 |

TABLE 9

| Sample Code | Percentage (%) | | | | | | | | | |
|---|---|---|---|---|---|---|---|---|---|---|
| | FFA | Esters | MG | DG | TG | Squalene | Sterols | Vitamin E | Carotenes | Weight (g) |
| Filtrate (Starting materials) | 3.0 | 0.0 | 0.0 | 0.0 | 4.8 | 30.0 | 35.9 | 26.2 | 0.2 | 0.34 |
| Hexane Layer | 1.2 | 0.0 | 0.0 | 0.0 | 9.3 | 44.2 | 27.1 | 17.1 | 0.2 | 0.22 |
| MeOH Layer | 4.3 | 0.0 | 0.0 | 0.0 | 0.8 | 5.4 | 38.1 | 51.2 | 0.1 | 0.10 |

TABLE 10

| Sample Code | Percentage (%) | | | | | | | | | |
|---|---|---|---|---|---|---|---|---|---|---|
| | FFA | Esters | MG | DG | TG | Sterols | Squalene | Vitamin E | Carotenes | Weight (g) |
| Filtrate | 8.56 | 0.00 | 0.00 | 0.00 | 0.00 | 18.20 | 36.55 | 36.70 | 0.30 | 0.60 |
| Hexane 1 | 3.12 | 0.00 | 0.00 | 0.00 | 0.00 | 8.78 | 69.10 | 19.00 | 0.20 | 0.25 |
| Hexane 2 | 4.00 | 0.00 | 0.00 | 0.00 | 0.00 | 11.72 | 54.12 | 30.16 | 0.30 | 0.12 |
| Hexane 3 | 1.57 | 0.00 | 0.00 | 0.00 | 0.00 | 8.70 | 77.21 | 12.52 | 0.30 | 0.19 |
| Methanol 1 | 9.92 | 0.00 | 0.00 | 0.00 | 0.00 | 15.10 | 18.18 | 56.80 | 0.20 | 0.31 |
| Methanol 2 | 1.69 | 0.00 | 0.00 | 0.00 | 0.00 | 13.85 | 5.12 | 79.33 | 0.20 | 0.10 |
| Methanol 3 | 0.01 | 0.00 | 0.00 | 0.00 | 0.00 | 22.10 | 18.37 | 59.52 | 0.10 | 0.04 |

The invention claimed is:

1. A method of extraction of phytosterols, squalene and vitamin E from crude palm oil comprising the steps of:
   a) conversion of the crude palm oil into palm oil methyl esters;
   b) performing three stages of short path distillation on the crude palm oil methyl esters obtained in step a) to yield a phytonutrient concentrate;
   c) saponification of the phytonutrient concentrate from step b) to give a saponified product;
   d) crystallization of phytosterols obtained in step c); and
   e) solvent partitioning of vitamin E and squalene from the remaining saponified product following said crystallization;
   wherein each of the three stages of short path distillation produces a distillate and a residue and wherein the third stage short path distillation is carried out on the distillate produced in the second stage short path distillation.

2. The method as claimed in claim 1, wherein the crude palm oil is converted directly into palm oil methyl esters.

3. The method as claimed in claim 1, wherein unsaponifiable matter is solvent extracted from the saponified product obtained in step c) and phytosterols are crystallized from the unsaponifiable matter.

4. The method as claimed in claim 3, wherein the unsaponifiable matter is mixed with a hydrocarbon solvent, short chain alcohol and water to give a mixture and crystallizing phytosterols from the mixture to give crystallized phytosterols and a remaining mixture.

5. The method as claimed in claim 4, wherein the unsaponifiable matter is mixed with a hydrocarbon solvent, short chain alcohol and water to form a mixture, wherein the hydrocarbon solvent, short chain alcohol and water are in a ratio by volume of 25:1:1 and wherein the mixture is heated to a temperature of 65° C. to 85° C. and slowly cooled to a temperature of 10° C. to 30° C. to crystallize the phytosterols.

6. The method as claimed in claim 4, wherein the remaining mixture is dried and then mixed with a hydrocarbon solvent and a short chain alcohol to partition the squalene into a hydrocarbon layer and the vitamin E into an alcohol layer.

7. The method as claimed in claim 6, wherein hexane and methanol is used to partition the squalene and the vitamin E.

8. The method as claimed in claim 6, wherein the hydrocarbon solvent and short chain alcohol used to partition squalene and the vitamin E are in a ratio by volume of 5:3.

9. The method as claimed in claim 1, wherein step (b) proceeds as follows:
   a. the first stage short path distillation is carried out on crude palm oil methyl esters;
   b. the second stage short path distillation is carried out on the residue of the first stage short path distillation;
   c. the third stage short path distillation is carried out on the distillate of the second stage short path distillation to yield a phytonutrients concentrate as a residue.

10. The method as claimed in claim 9, wherein the second stage short path distillation is carried out at a temperature of 130° C. to 200° C. and pressure less than 1 mTorr.

11. The method as claimed in claim 10, wherein the first stage short path distillation is carried out at a temperature of 70° C. to 120° C. and pressure between 10 mTorr to 50 mTorr and the third stage short path distillation is carried out at a temperature below 120° C. and pressure less than 1 mTorr.

12. The method as claimed in claim 1, wherein a hydrocarbon solvent and a short chain alcohol are used in step e) to partition the squalene into a hydrocarbon layer and the vitamin E into an alcohol layer.

13. The method as claimed in claim 12, wherein hexane and methanol are used in step e) to partition the squalene into a hexane layer and the vitamin E into a methanol layer.

14. The method of extraction of phytosterols, squalene and vitamin E from crude palm oil, comprising the steps of:
   i. conversion of crude palm oil into palm oil methyl esters;
   ii. Performing a first stage short path distillation on the crude palm oil methyl esters obtained in the step i, wherein the first stage short path distillation is carried out at a temperature of 70° C. to 120° C. and pressure between 10 mTorr to 50 mTorr;
   iii. Performing a second stage short path distillation on the residue obtained in the first stage short path distillation, wherein the second stage short path distillation is carried out at a temperature of 130° C. to 200° C. and pressure less than 1 mTorr;
   iv. Performing a third stage short path distillation on the distillate obtained in the second stage short path distillation, wherein the third stage short path distillation is carried out at a temperature below 120° C. and pressure less than 1 mTorr;
   v. saponification of the residue obtained the third stage short path distillation to give a saponified product;
   vi. solvent extraction of unsaponifiable matter from the saponified product obtained in step v;
   vii. mixing the unsaponifiable matter obtained in step vi with a hydrocarbon solvent, short chain alcohol and water to give a mixture;
   viii. crystallization of phytosterols from the mixture obtained in step vii to give crystallized phytosterols and a remaining mixture;
   ix. separating the crystallized phytosterols and drying the remaining mixture to give a dried mixture; and
   x. mixing the dried mixture obtained in step ix with a hydrocarbon solvent and a short chain alcohol to partition the squalene into a hydrocarbon layer and the vitamin E into an alcohol layer.

* * * * *